United States Patent [19]

Hendrickson et al.

[11] Patent Number: 5,641,144
[45] Date of Patent: Jun. 24, 1997

[54] DIALYZER HOLDER

[75] Inventors: Dan Lee Hendrickson, Golden; Jeff Samson, Boulder; Jim Zook, Denver, all of Colo.

[73] Assignee: COBE Laboratories, Inc., Lakewood, Colo.

[21] Appl. No.: 477,179

[22] Filed: Jun. 7, 1995

[51] Int. Cl.$^6$ .................................................. A61M 1/00
[52] U.S. Cl. ............................ 248/292.13; 248/311.2; 248/309.1; 604/322; 604/4; 128/DIG. 26
[58] Field of Search .......................... 248/292.13, 299.1, 248/304, 306, 311.2, 316.7, 500, 505, 309.1, 113; 604/322, 4, 5, 6, 174, 175, 176, 177, 178, 179, 180; D24/108, 128

[56] References Cited

U.S. PATENT DOCUMENTS

| | | | |
|---|---|---|---|
| 974,998 | 11/1910 | Sorensen | 248/113 |
| 1,494,777 | 5/1924 | Dodsworth | 248/113 |
| 3,161,393 | 12/1964 | Swanson | 248/113 |
| 3,323,772 | 6/1967 | Dupree et al. | 248/316.7 X |
| 4,498,983 | 2/1985 | Bilstad et al. | 604/6 X |
| 4,909,467 | 3/1990 | Shan-Pao | 248/113 X |

FOREIGN PATENT DOCUMENTS

| | | |
|---|---|---|
| 2310136 | 12/1976 | France . |
| 3642671 | 6/1988 | Germany . |
| 4313708 | 11/1994 | Germany . |
| 73181 | 11/1931 | Switzerland .................. 248/309.1 |
| 769425 | 3/1957 | United Kingdom ............ 248/113 |

*Primary Examiner*—Ramon O. Ramirez
*Assistant Examiner*—Brian J. Hamilla
*Attorney, Agent, or Firm*—John B. Phillips

[57] ABSTRACT

A dialyzer holder for quickly and securely fastening a variety of different dialyzers in position against a surface of a dialysis machine. The dialyzer holder includes an elongated arm pivotably attached to the dialysis machine. An attachment device for engaging a dialyzer is fixed to the free end of the pivotable elongated arm. The pivotable elongated arm is biased to direct the attachment device toward the dialysis machine, and the elongated arm is of sufficient length to position a dialyzer between the attachment device and the dialysis machine when an operator overcomes the bias force and pivots the arm away from the dialysis machine. The bias on the elongated arm is sufficiently strong to maintain the dialyzer suspended between the attachment device and the dialysis machine, even once the dialyzer is filled with blood and dialysate during patient treatment. Frictional pads placed on the dialysis machine and the attachment device may help to inhibit movement of the dialyzer once it is suspended between the dialysis machine and the attachment device. The attachment device is adapted to engage a variety of different styles and sizes of dialyzers without requiring any type of modification. An alternative attachment device may be used when the dialyzer holder is primarily used with conventional hollow fiber dialyzers and plate dialyzers.

20 Claims, 6 Drawing Sheets

DIALYZER HOLDER

The present invention relates to a new and improved dialysis machine and a holding mechanism for temporarily attaching different types of dialyzers to the dialysis machine, including hollow fiber dialyzers and plate dialyzers.

BACKGROUND OF THE INVENTION

A dialysis machine is used as a substitute for the natural kidney functions of a human body. As such, the dialysis machine cleans the blood of the natural accumulation of bodily wastes by separating the wastes from the blood outside or extracorporeally of the body. The separated wastes are discharged and the cleansed blood is returned to the body.

A dialysis machine uses a dialyzer to separate the wastes from the blood. The dialyzer includes a porous membrane located within a closed housing which effectively separates the housing into separate blood and dialysate compartments. The blood removed from the patient flows through the blood compartment, while a prepared solution of dialysate is passed through the dialysate compartment. The wastes from the blood pass through the membrane by osmosis, ionic transfer or fluid transport into the dialysate and, depending upon the type of dialysis treatment, desirable components from the dialysate may pass in the opposite direction through the membrane and into the blood. The transfer of the wastes into the dialysate cleanses the blood while allowing the desired components from the dialysate to enter the bloodstream.

The transfer of blood between the patient and the dialyzer occurs within a disposable blood tubing set. The blood tubing set and the dialyzer represent a closed extracorporeal path through which the patient's blood travels. The blood tubing set includes an arterial line for drawing blood from a patient, a venous line for returning blood to the patient, and a number of other lines for connecting the arterial and venous lines to the dialyzer and a blood pump.

Two types of dialyzers commonly used in dialysis treatments include the hollow fiber dialyzer and the plate dialyzer. The hollow fiber dialyzer is typically formed from a cylindrical housing having a bundle of hollow microporous fibers extending between opposing ends of the housing. The microporous nature of the fibers allows blood to flow through the hollow interior of the fibers without passing through the walls of the fibers. The hollow fibers are sealed or potted at each end of the housing so that the open ends of the hollow fibers communicate with a blood manifold at each end of the housing, one manifold connected to a blood inlet and the other manifold connected to a blood outlet. The interior volume of the hollow fibers between the inlet and outlet manifolds thus collectively comprise the blood compartment of the dialyzer. A separate inlet and outlet on the cylindrical housing (between the blood manifolds) provides access for dialysate to enter and exit the cylindrical housing. The dialysate enters the housing through the inlet and flows around the hollow fibers in the area between the sealed blood manifolds. The area within the housing between the manifolds which is not consumed by the hollow fibers thus comprises the dialysate compartment. The microporous nature of the hollow fibers allows for the exchange of wastes and other desired components between the blood and the dialysate. The used dialysate is then pumped from the dialyzer while the cleansed blood is collected within the outlet manifold and returned to the patient.

The plate dialyzer typically includes a rectangular housing within which a plurality of membrane plates are stacked together, or within which a single membrane is folded over upon itself a number of times, so that the blood and dialysate compartments are defined on opposite sides of the adjoining plates. A blood inlet and outlet are positioned to communicate with the respective sides of the plates that define the blood compartment, while a dialysate inlet and outlet are positioned to communicate with the dialysate compartment defined by the opposite sides of the plates.

Although the hollow fiber dialyzer is typically more expensive to manufacture than the plate dialyzer, the hollow fiber dialyzer is used predominantly in the United States because it can be cleaned and reused with a single patient a number of times, thereby reducing the effective cost of each dialysis treatment. Due to the intricate flow path between the plates of a plate dialyzer, it is not currently feasible to clean and reuse a plate dialyzer. The cost per dialysis treatment is thus higher with a plate dialyzer than with a reusable hollow fiber dialyzer. However, in countries where a patient's dialysis treatment is subsidized or paid for by the government, plate dialyzers may frequently be used and disposed of as medical waste after each treatment. Additionally, as the cost of plate dialyzers drops, and due to other concerns associated with cleaning hollow fiber dialyzers (e.g., the man hours required to clean the dialyzers and environmental concerns relating to the chemical sterilants used in cleaning the dialyzers), the popularity of plate dialyzers has recently risen. Therefore, to provide hospitals and dialysis clinics with the freedom to choose the type of dialyzer which best suits their needs, and to provide them with the flexibility to change their choice as their needs change, it will be increasingly important for dialysis machines to accommodate both types of dialyzers. Furthermore, it is desireable for dialysis machines to accomodate other types of devices used in extracorporeal treatments, for example a hemo-perfusion cartridge or filter.

Present dialysis machines are typically designed to hold only one type of dialyzer, usually either a hollow fiber or a plate dialyzer. For example, the majority of dialysis machines sold in the United States include a simple receptacle for holding a hollow fiber dialyzer and do not include any means for conveniently holding a plate dialyzer. Force fitting a rectangular plate dialyzer into a receptacle for a cylindrical hollow fiber dialyzer could lead to a serious accident should the plate dialyzer become dislodged and damaged during treatment.

Some dialysis machines have been retrofitted to remove the receptacle for a hollow fiber dialyzer and replace it with a receptacle for a plate dialyzer (or vice-versa). However, such a replacement is difficult and is usually only undertaken when a hospital or dialysis clinic that has used substantially only one type of dialyzer converts to using the other type of dialyzer. Replacing or converting the dialyzer holders on each dialysis machine would not be feasible for clinics that may routinely use both types of dialyzers. Alternatively, some dialysis machines have been retrofitted with a second attachment device for holding a plate dialyzer or a hollow fiber dialyzer. However, these type of aftermarket fixes do not typically function well and, furthermore, producing both types of dialyzer holders represents an extra cost to dialysis machine manufacturers.

Thus, while a number of different types and sizes of dialyzers are currently available for use in dialysis treatments, hospitals and clinics are not always able to benefit from these advances due to the incompatibility of existing dialysis machines with the new dialyzers. Additionally, a similar incompatibility may exist with other types of devices used in extracorporeal treatments (e.g., a hemo-perfusion cartridge).

These and other considerations have contributed to the evolution of the present invention which is summarized below.

SUMMARY OF THE INVENTION

One of the significant aspects of the present invention pertains to a new dialyzer holder for attaching a dialyzer to a dialysis machine. Another significant aspect of the present invention relates to a dialyzer holder which quickly and securely attaches a dialyzer to a dialysis machine. A further significant aspect of the present invention relates to providing a single dialyzer holder on a dialysis machine which is equally adept at holding either a hollow fiber dialyzer or a plate dialyzer. A further significant aspect of the present invention pertains to using a single dialyzer holder to attach a wide variety of dialyzers and other extracorporeal treatment devices to a dialysis machine without having to reconfigure or modify the dialyzer holder.

In accordance with these and other aspects, the present invention may be generally summarized as a dialyzer holder for temporarily securing a dialyzer or other extracorporeal treatment device (e.g., a hemo-perfusion cartridge) to a surface of a dialysis machine. The dialyzer holder includes an elongated arm having a first end pivotably attached to the dialysis machine to selectively pivot a second end of the arm relative to a surface of the dialysis machine. Additionally, an attachment device for contacting the dialyzer is fixed to the second end of the arm. The attachment device is primarily adapted to engage either a hollow fiber dialyzer or a plate dialyzer, although a variety of other types of dialyzers may also be engaged by the attachment device.

The elongated arm is sufficiently long to allow the second end to be pivoted away from the surface of the dialysis machine so that a dialyzer may be positioned between the attachment device and the dialysis machine. Furthermore, the pivotable elongated arm is attached to a spring or other biasing device so that the second end of the arm and the attachment device are biased toward the surface of the dialysis machine. The bias on the elongated arm is sufficiently strong to hold a dialyzer suspended between the attachment device and the surface of the dialysis machine, yet the bias may be overcome by a dialysis machine operator who must lift the second end of the arm and position the dialyzer between the attachment device and the dialysis machine.

The dialyzer holder also preferably includes one or more frictional pads attached to the surface of the dialysis machine to contact the dialyzer and help prevent the dialyzer from moving in relation to the dialysis machine once the attachment device has engaged the dialyzer. The attachment device also preferably includes a frictional surface for engaging the dialyzer and preventing the dialyzer from moving relative to the dialyzer holder once the dialyzer is suspended between the attachment device and the dialysis machine.

A more complete appreciation of the present invention and its scope may be obtained from the accompanying drawings, which are briefly summarized below, from the following detailed descriptions of presently preferred embodiments of the invention, and from the appended claims.

DETAILED DESCRIPTION

Figure 1:
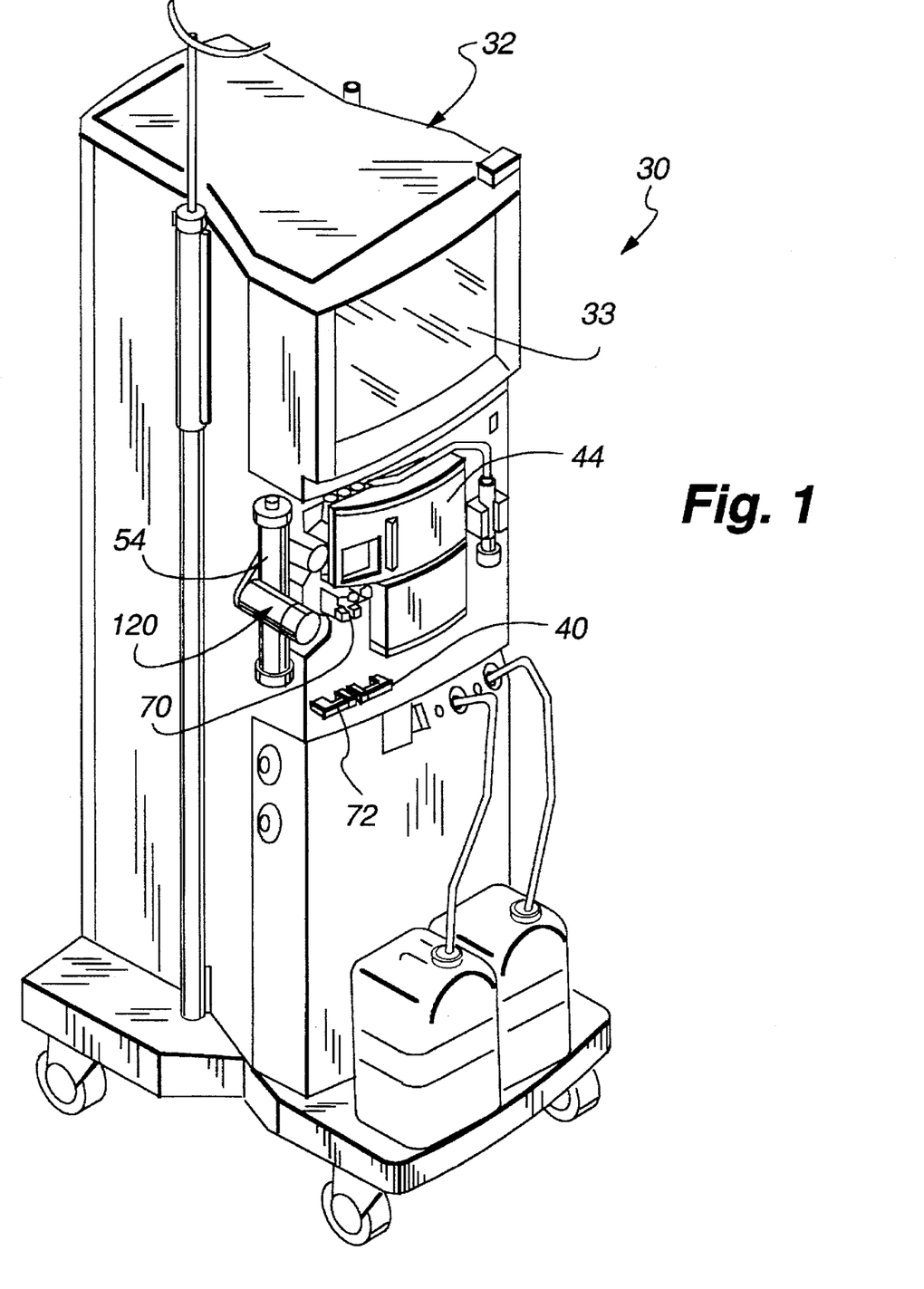
FIG. 1 is a perspective view of a dialysis machine which incorporates the present invention.
Figure 2:
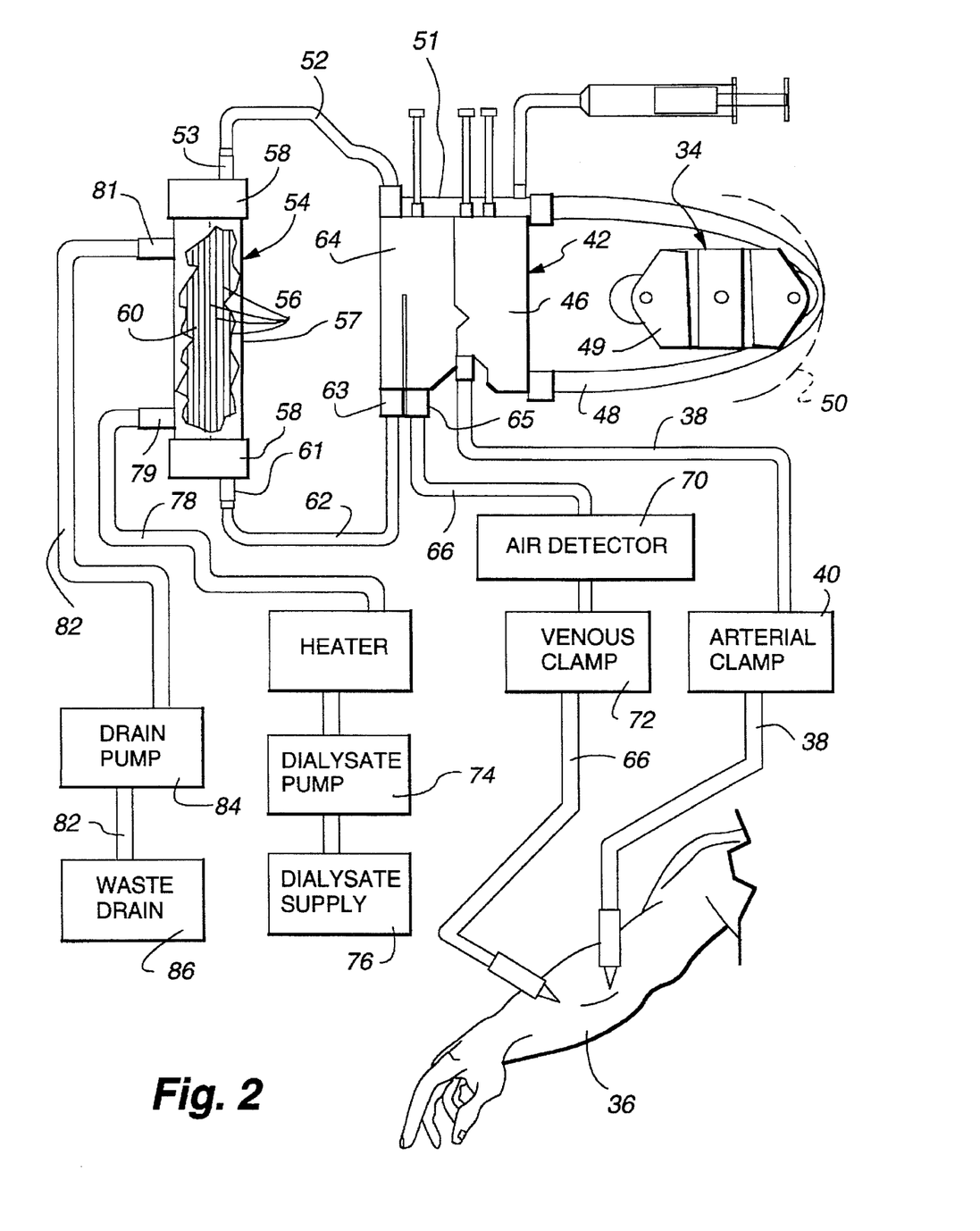
FIG. 2 is a generalized view illustrating a hollow fiber dialyzer, an extracorporeal blood flow path from a patient through the dialyzer, and a dialysate flow path through the dialyzer, as are present during treatment of a patient with the dialysis machine shown in FIG. 1.

An example of a dialysis machine with which the present invention may be advantageously employed is shown at 30 in FIG. 1. The dialysis machine 30 includes an enclosure 32 to which are attached, or within which are housed, those functional devices and components of the dialysis machine 30 which are generally illustrated in FIG. 2. The enclosure 30 also includes a conventional input/output ("I/O") device for controlling the machine 30, such as a touch-screen monitor 33 as shown in FIG. 1.

The dialysis machine 30 includes at least one blood pump 34 which controls the flow of blood from a patient 36. An arterial line or tubing 38 is connected through an arterial clamp 40 to a blood handling cartridge 42. The blood pump 34 and the blood handling cartridge 42 are normally retained behind a door 44 (FIG. 1) of the machine 30, and thus are not shown in FIG. 1. The blood pump 34 is typically a peristaltic pump.

Blood from the patient 36 flows through an extracorporeal flow circuit when the arterial clamp 40 is open and the blood pump 34 draws blood from the patient 36. The blood passes through the arterial line 38 and into an arterial reservoir 46 of the cartridge 42. The blood pump 34 draws blood from the arterial reservoir 46 through a pump tubing 48 which is squeezed or pinched by a rotating rotor 49 against a stationary raceway 50, in the typical manner of peristaltic pumps. The blood within the pump tubing 48 which is rotationally in front of the rotor 49 is propelled through the pump tubing 48 and into a manifold 51 of the cartridge 42. A tubing 52 conducts the blood from the manifold 51 of the cartridge 42 into a blood inlet 53 of a hollow fiber dialyzer 54.

The hollow fiber dialyzer 54 includes a plurality or bundle of hollow micro-porous fibers 56 which run the length of a cylindrical housing 57 (FIG. 2). The hollow fibers 56 are sealed or "potted" adjacent each end of the housing 57 so that the open ends of the fibers extend between the sealant and the ends of the housing, and caps 58 are sealed to each end of the housing 57 to form blood reservoirs in fluid communication with the open ends of the hollow fibers 56. The collective volume of the hollow fibers 56 defines a blood chamber within the dialyzer 54, while the space between the hollow fibers 56 (shown greatly exaggerated in FIG. 2) defines a dialysate chamber 60 between the ends of the dialyzer cylindrical housing 57. The construction of hollow fiber dialyzers 54 is well known to those skilled in the art.

As the patient's blood passes through the dialyzer 54, the waste products within the blood pass out of the microporous material defining the hollow fibers 56 where the waste products mix with the dialysate in the chamber 60. The cleansed blood exits the dialyzer 54 through a blood outlet 61 in the cap 58 and is then transferred through a tubing 62 to an inlet 63 of a venous reservoir 64. Any air which might have been unintentionally introduced into the blood is collected and removed while the blood is in the venous reservoir 64. Blood exits the venous reservoir 64 through an outlet 65 and is removed from the cartridge 42 through a venous tubing or line 66.

After leaving the venous reservoir 64, the blood flows through the venous line 66 to an air detector 70. If an excessive or dangerous amount of air is present in the venous line 66, a venous line clamp 72 will immediately close to terminate the flow of blood through the venous line 66 before the detected air reaches the patient 36.

The enclosure 32 of the dialysis machine 30 also encloses the various elements of a dialysate flow path, shown in abbreviated form in FIG. 2. The elements of the dialysate flow path include a number of different valves (most of which are not shown) and a dialysate pump 74 which draws dialysate from a container or from an internal supply 76 of dialysate which the dialysis machine 30 has prepared from appropriate chemicals and a supply of purified water.

The dialysate pump 74 draws the dialysate from the supply 76 and delivers the dialysate through a dialysate supply tubing or line 78 to an inlet 79 of the dialysate chamber 60 of the dialyzer 54. The dialysate flows past and around the hollow micro-porous fibers 56 where it absorbs the waste products from the blood traveling through the hollow fibers 56. Any beneficial components within the dialysate which are desired to be transferred to the blood pass through the microporous material that defines hollow fibers 56 and enter the blood.

Dialysate containing the waste products exits the dialysate chamber 60 through an outlet 81 and is removed from the dialyzer 54 through a dialysate waste tubing or line 82 by operation of a drain pump 84. The dialysate removed from the dialyzer 54 is delivered through the waste tubing 82 to a waste drain 86. The waste drain 86 may be a separate container which receives the used dialysate and accumulated waste products, or it may simply be a drain to a public sewer.

The reservoirs 46 and 64 and the manifold 51 of the blood handling cartridge 42, together with the tubes 38, 48, 52, 62 and 66, are collectively referred to as a blood tubing set ("BTS"). The BTS is disposable and is typically thrown away after each dialysis treatment. Similarly, the hollow fiber dialyzer 54 may be used as a disposable product, although it is not uncommon for a hollow fiber dialyzer to be reused with a single patient. The dialyzer 54 will typically be reused by a patient who regularly visits the same clinic for dialysis treatments. Following each treatment, the hollow fiber dialyzer 54 is cleaned with a sterilant and is then stored until the patient's next visit to the clinic. The dialyzer 54 must then be thoroughly cleaned before use to ensure that the sterilant is not transferred to the patient's bloodstream during the next dialysis treatment.

Figure 6:
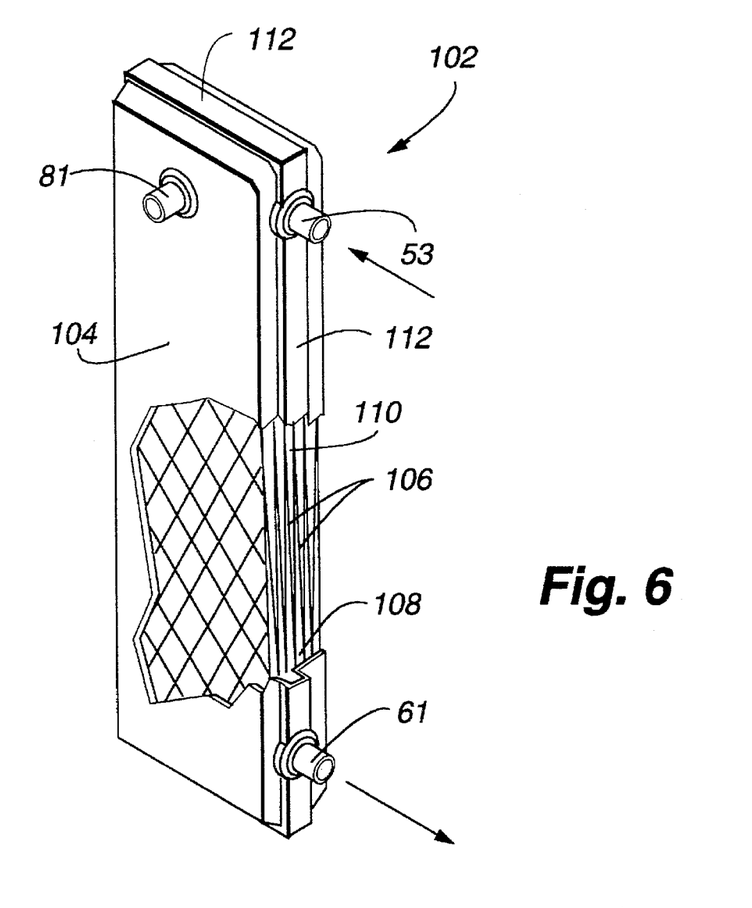
FIG. 6 is a perspective view of a plate dialyzer with portions broken away to show internal details.
Figure 7:
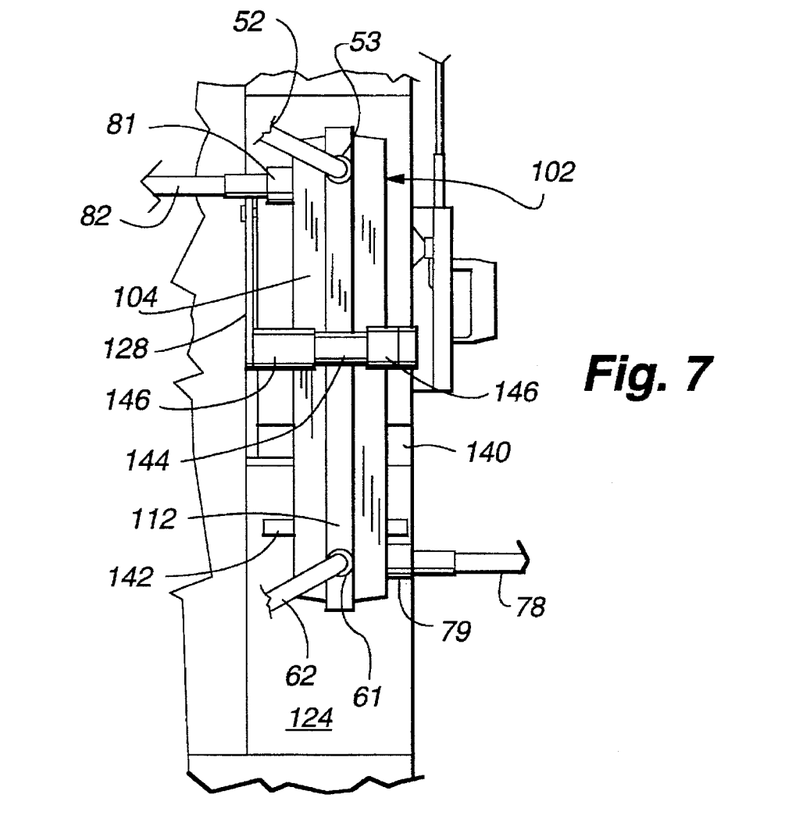
FIG. 7 is a partial side view of the dialysis machine shown in FIG. 1, illustrating the dialyzer holder of the present invention supporting a plate dialyzer.
Figure 8:
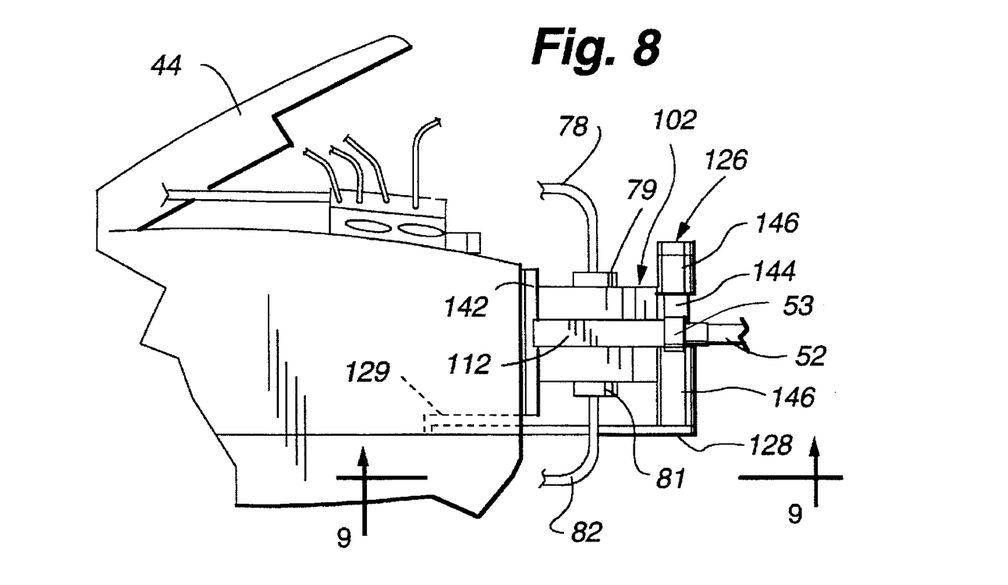
FIG. 8 is a partial top view of the dialysis machine and the plate dialyzer shown in FIG. 7.

The dialysis machine 30 operates in the manner described above regardless of whether it is used with the hollow fiber dialyzer 54 or a plate dialyzer 102 (FIGS. 6–8). The plate dialyzer 102 is a disposable product formed by a rectangular housing 104 with a number of membrane plates 106 connected together in such a manner that a blood compartment 108 and a dialysate compartment 110 are defined within the housing 104 (FIG. 6). Alternatively, a single membrane may be folded a number of times within the housing 104 to form the blood compartment 108 on one side of the membrane and the dialysate compartment on the opposite side of the membrane. The plate dialyzer 102 includes the blood inlet 53 and outlet 61 connected to the blood compartment 108, as well as the dialysate inlet 79 and outlet 81 connected to the dialysate compartment 110.

Pressure applied directly to the housing 104 of the plate dialyzer 102 tends to compress the plates 106 upon one another, thereby decreasing the effective size of the blood and dialysate compartments 108 and 110 and inhibiting the effectiveness of the plate dialyzer 102. Thus, the plate dialyzer 102 further includes a guard structure 112 which extends around the perimeter of the rectangular housing 104. The guard structure 112 is typically made of a hard plastic material to resist bending and functions to prevent pressure from being applied directly to the housing 104 when the plate dialyzer is attached to the dialysis machine 30. The construction of plate dialyzers is well known to those skilled in the art.

The present invention relates to a dialyzer holder 120 attached to the enclosure 32 of the dialysis machine 30 for releasably attaching both hollow fiber dialyzers 54 and plate dialyzers 102 (as well as other extracorporeal treatment devices such as a hemo-perfusion cartridge). The dialyzer holder 120 pivots out from a recessed position within the enclosure 32 and is biased to hold a dialyzer against a side surface 124 of the enclosure 32.

Figure 9:
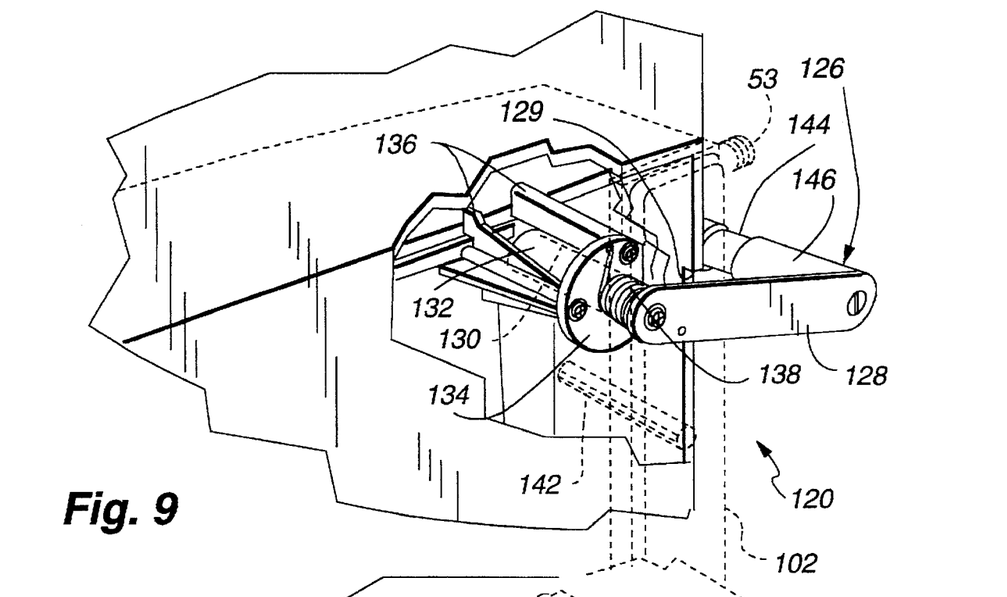
FIG. 9 is a partial perspective view taken substantially in the plane of point of view line 9—9 in FIG. 8, with a portion broken away to show internal details.
Figure 10:
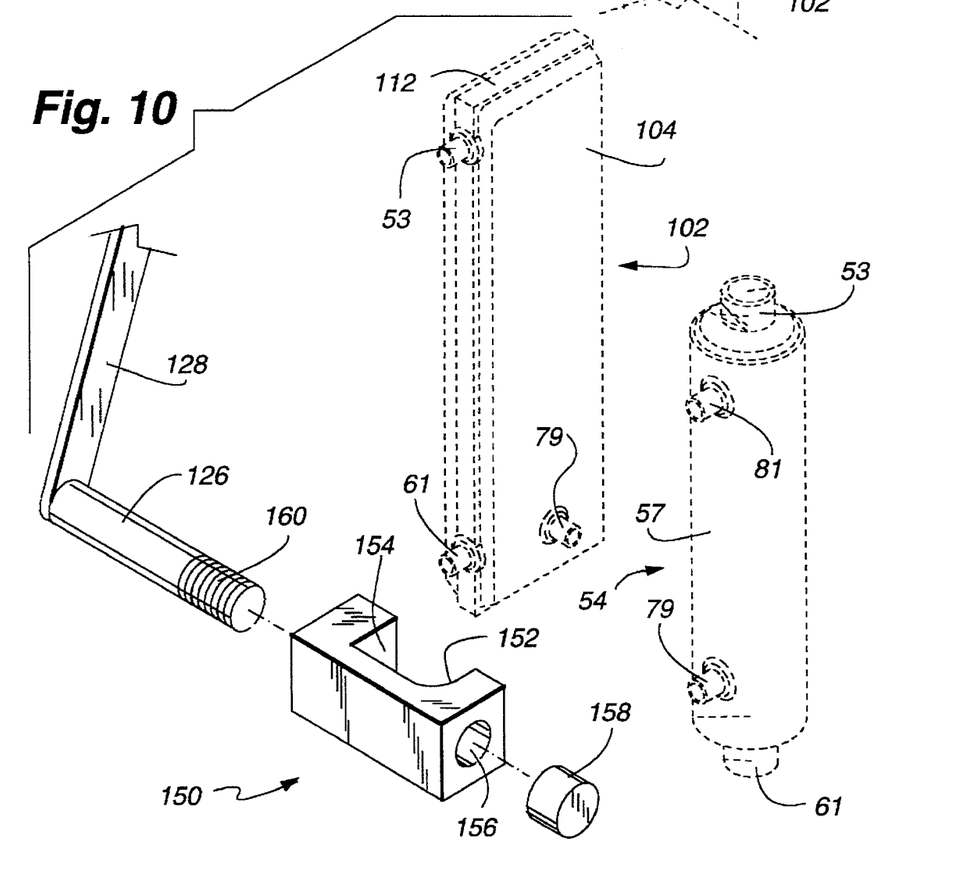
FIG. 10 is a perspective view of an alternate embodiment of an attachment device of the dialyzer holder of the present invention, shown in relation to both a plate dialyzer and a hollow fiber dialyzer illustrated in phantom.

The dialyzer holder 120 includes a capture rod 126 attached at a right angle to one end of a pivot arm 128, as shown in FIG. 10. The capture rod 126 and pivot arm 128 are preferably made of metal for high strength and durability. The opposite end of the pivot arm 128 extends within a slot 129 (FIGS. 5, 8 and 9) formed within the enclosure 32 and is fixed to one end of a shaft 130. The shaft 130 protrudes from the enclosure 32 and enters the slot 129 at a right angle to the plane of the slot 129 to attach perpendicularly to the pivot arm 128 (FIG. 9). The opposite end of the shaft 130 is rotatably attached within a cylindrical shaft housing 132. A circular flange 134 fixed to the end of the shaft housing 132 is attached to two or more ribs 136 formed within the enclosure 32 (FIG. 9) to fix the shaft housing 132 relative to the enclosure 32.

Figure 3:
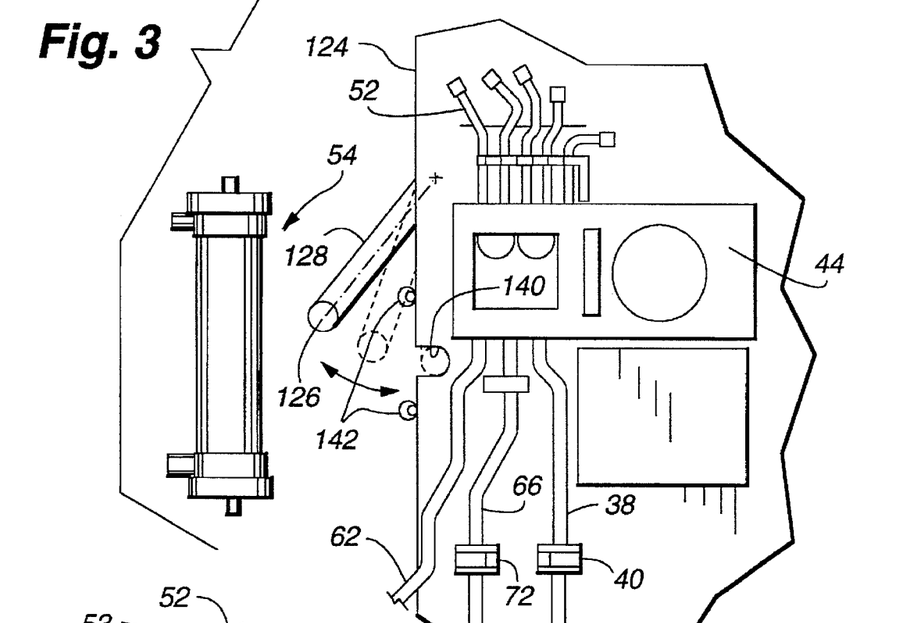
FIG. 3 is a partial front view of the dialysis machine shown in FIG. 1, illustrating the dialyzer holder of the present invention in three different positions relative to the dialysis machine.

A coil torsion spring 138 is preferably wrapped about the shaft 130 between the circular flange 134 and the pivot arm 128. The spring 138 is attached at one end to the shaft 130 and at the other end to the fixed flange 134 to provide a clockwise rotational bias to the shaft 130 and the attached pivot arm 128, as viewed from the rear of the dialysis machine 30 in FIG. 9. The torsion spring 138 biases the capture rod 126 in the downward direction so that the capture rod 126 tends to rest against the side surface 124 of the dialysis machine 30, as shown in FIG. 3. A recessed groove 140 in the side surface 124 allows the capture rod 126 to rest flush with the side surface 124 (FIG. 3) when the dialyzer holder 120 is not holding a dialyzer. The recessed position of the capture rod 126 within the side surface 124 of the enclosure 32 prevents the dialyzer holder 120 from protruding from the enclosure where it could possibly be damaged during movement of the dialysis machine 30.

Figure 4:
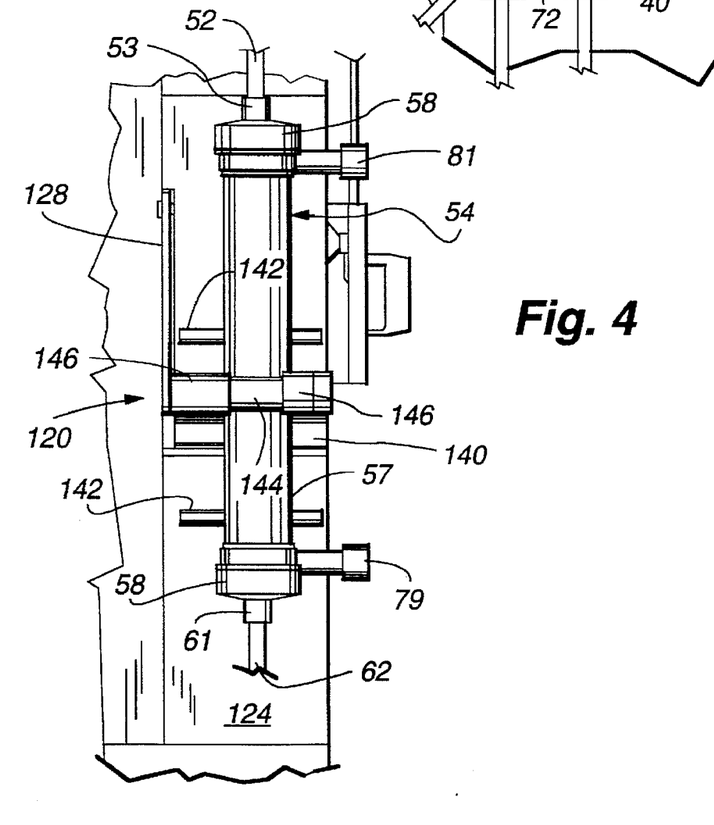
FIG. 4 is a partial side view of the dialysis machine shown in FIG. 1, illustrating the dialyzer holder of the present invention supporting a hollow fiber dialyzer.

The dialyzer holder 120 operates to hold a dialyzer (or other extracorporeal treatment device) against the side surface 124 of the dialysis machine 30. A dialysis machine operator lifts the capture rod 126 from its recessed position within the groove 140 (FIG. 3) by pivoting the pivot arm 128 against the bias of the torsion spring 138. A dialyzer is then positioned against the side surface 124 and the capture rod 126 is lowered to contact the dialyzer and press it firmly against the side surface 124 under the force of the torsion spring 138. Friction pads 142 attached to the side surface 124 of the enclosure 32 grip the dialyzer on the opposite side of the capture rod 126 and enhance the hold of the dialyzer holder 120. The friction pads 142 are preferably made of silicone rubber and are preferably detachable from the side surface 124 for ease of cleaning (two pads 142 are shown in FIGS. 3 and 4, one on each side of the groove 140, although additional pads may be utilized). Additionally, the capture rod 126 preferably includes a central friction surface 144 for contacting the dialyzer. The central friction surface 144 is preferably a silicone rubber pad wrapped about the middle of the preferably round capture rod 126. Furthermore, non-frictional centering guides 146 at each end of the capture rod 126 help to position the dialyzer so that it contacts the central friction surface 144 when the dialyzer is loaded between the dialyzer holder 120 and the side surface 124.

Figure 5:
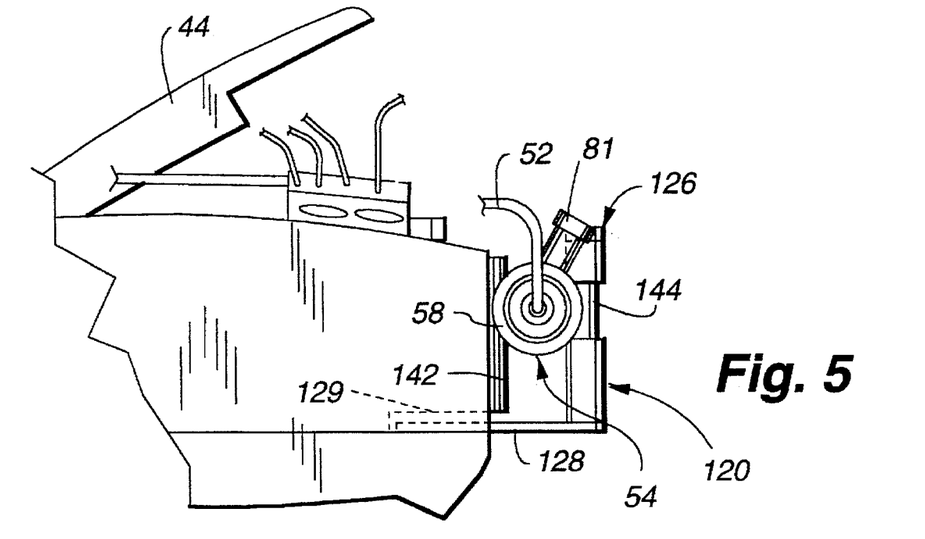
FIG. 5 is partial top view of the dialysis machine and the hollow fiber dialyzer shown in FIG. 4.

FIGS. 1, 4 and 5 illustrate the dialyzer holder 120 holding a hollow fiber dialyzer 54 against the side surface 124 of the dialysis machine 30. The central friction surface 144 contacts the cylindrical housing 57 on one side of the dialyzer 54, while the friction pads 142 contact the opposite side of the cylindrical housing 57. Contacting the housing 57 in this manner does not restrict the flow of either blood or dialysate within the hollow fiber dialyzer 54 due to the axial flow of fluid through the dialyzer and the relatively rigid nature of the housing 57.

FIGS. 7 and 8 illustrate the dialyzer holder 120 holding a plate dialyzer 102 against the side surface 124 of the dialysis machine 30. In this instance, the central friction surface 144 of the capture rod 126 contacts the guard structure 112 on one side of its rectangular perimeter, while the friction pads 142 on the side surface 124 contact the guard structure 112 on the opposite side of its perimeter. By contacting the plate dialyzer 102 only along its relatively rigid guard structure 112, the dialyzer holder 120 does not compress the housing 104 of the plate dialyzer 102 and thus does not restrict the flow between the membrane plates 106 within the housing 104.

The torsion spring 138 provides a sufficient bias force to hold the dialyzer against the side surface 124, even when the dialyzer is filled with blood and dialysate during treatment of a patient. Thus, the frictional engagement of the pads 142 and the central surface 144 of the capture rod 126 under the pressure of the torsion spring 138 is sufficient to overcome the weight of the filled dialyzer. However, if a tighter or more snug grip between the capture rod 126 and the dialyzer is desired, an alternative attachment block 150 (FIG. 10) may be fitted to the capture rod 126. The alternative attachment block 150 is formed from frictional material, preferably silicone rubber, and is molded or cut out to define a rounded end 152 and a square end 154. A bore hole 156 formed through the attachment block 150 allows the block to fit over the capture rod 126, and a screw cap 158 is preferably attached to a threaded end 160 of the capture rod 126 to fix the position of the block 150 relative to the capture rod.

The attachment block 150 is thus shaped to provide more than a single-point contact with both the cylindrical hollow fiber dialyzer 54 and the rectangular plate dialyzer 102. For example, the hollow fiber dialyzer 54 could be positioned against the round end 152 so that the attachment block 150 grips a portion of the circumference of the cylindrical housing 57, while the plate dialyzer 102 could be positioned against the square end 154 so that the attachment block 150 grips both the guard structure 112 and a portion of the rectangular housing 104. It is important to realize that the vast majority of the force applied to the plate dialyzer 102 is still applied to the rigid guard structure 112 and that the contact of the square end 154 with the less rigid housing 104 serves mainly as a back-up so that the square end 154 does not apply a force sufficient to compress the membrane plates 106 within the housing 104 (FIG. 6).

The main benefit of the dialyzer holder 120 is its ability to hold a dialyzer of any shape and size against the side of a dialysis machine. Thus, both hollow fiber and plate dialyzers may be interchanged on the same dialysis machine 30, and both may be attached to the machine with equal ease. Additionally, although the dialyzer holder 120 has been discussed in relation to only cylindrical and rectangular dialyzers, it should be apparent to one skilled in the art that dialyzers or other extracorporeal treatment devices (such as a hemo-perfusion cartridge) having non-conventional shapes could be held with equal ease.

Furthermore, any dialyzer may be very quickly attached to and removed from the machine by simply raising the capture rod 126 against the force of the torsion spring 138. The dialyzer holder 120 does not include any fasteners which may break or which may be incorrectly attached by a dialysis machine operator. Thus, the operator can be assured that the dialyzer is properly attached as soon as he or she positions the dialyzer on the friction pads 142 and releases the capture rod 126.

A presently preferred embodiment of the present invention and many of its improvements have been described with a degree of particularity. This description is a preferred example of implementing the invention, and is not necessarily intended to limit the scope of the invention. The scope of the invention is defined by the following claims.

The invention claimed is:

1. A dialysis machine having an improved dialyzer holder, said dialyzer holder comprising:

an elongated arm having a first end pivotably attached to the dialysis machine and a second end adapted to selectively pivot away from and toward a surface of the dialysis machine, said elongated arm having a length sufficient to allow the second end to pivot away from the surface of the dialysis machine a sufficient distance to position a dialyzer between the second end and the surface of the dialysis machine;

an attachment device connected to the second end of the elongated arm and extending substantially transverse to the elongated arm to contact the dialyzer; and means biasing the second end of the elongated arm toward the surface of the dialysis machine to suspend the dialyzer against the surface of the dialysis machine when the dialyzer is positioned between the attachment device and the surface of the dialysis machine.

2. A dialysis machine as defined in claim 1 wherein the attachment device is adapted to fit within a recessed area in the surface of the dialysis machine when the dialyzer is not positioned between the attachment device and the surface of the dialysis machine.

3. A dialysis machine as defined in claim 1, further comprising:

a friction pad positioned on the surface of the dialysis machine to contact the dialyzer and inhibit movement of the dialyzer along the surface of the dialysis machine.

4. A dialysis machine as defined in claim 1, further comprising:

two friction pads positioned on the surface of the dialysis machine to contact the dialyzer at two separate points and inhibit movement of the dialyzer along the surface of the dialysis machine.

5. A dialysis machine as defined in claim 1 wherein the attachment device includes a padded surface adapted to contact the dialyzer and inhibit relative movement between the attachment device and the dialyzer.

6. A dialysis machine as defined in claim 5 wherein the attachment device further comprises:

an elongated rod having a first end fixed to the second end of the elongated arm.

7. A dialysis machine as defined in claim 6 wherein the padded surface is wrapped around a central portion of the elongated rod.

8. A dialysis machine as defined in claim 6 wherein the attachment device further comprises:

a first centering guide positioned between the first end of the elongated rod and the padded surface; and a second centering guide positioned between the padded surface and a second end of the elongated rod, said centering guides adapted to align the dialyzer with the padded surface when the dialyzer is positioned between the attachment device and the surface of the dialysis machine.

9. A dialysis machine as defined in claim 8 wherein the biasing means comprises a torsion spring.

10. A dialysis machine as defined in claim 3 wherein the attachment device includes a padded surface adapted to contact a hollow fiber dialyzer and inhibit relative movement between the attachment device and the hollow fiber dialyzer.

11. A dialysis machine as defined in claim 3 wherein the attachment device includes a padded surface adapted to contact a plate dialyzer and inhibit relative movement between the attachment device and the plate dialyzer.

12. A dialysis machine as defined in claim 3 wherein the attachment device includes a padded surface adapted to contact one of a hollow fiber dialyzer and a plate dialyzer and inhibit relative movement between the attachment device and one of the hollow fiber and plate dialyzer.

13. A dialysis machine as defined in claim 12 wherein the attachment device further comprises:

an elongated rod having a first end fixed to the second end of the elongated arm, said elongated rod extending substantially transverse to the elongated arm; and a rubber block attached to the elongated rod, said rubber block having a rear wall for contacting one of the hollow fiber dialyzer and plate dialyzer, and said rubber block further having a first end wall for contacting the plate dialyzer and a second end wall opposite the first end wall for contacting the hollow fiber dialyzer.

14. A dialysis machine as defined in claim 1 further comprising:

a shaft rotatably attached to the dialysis machine; and wherein:

the first end of the elongated arm is attached to the shaft and extends substantially transverse to the shaft; and the biasing means comprises a torsion spring wrapped around the shaft, said torsion spring having a first end attached to the dialysis machine and a second end attached to the shaft to apply a torsional bias to the shaft and the attached elongated arm.

15. A dialysis machine as defined in claim 2, further comprising:

a first friction pad positioned on the surface of the dialysis machine adjacent one end of the recessed area;

a second friction pad positioned on the surface of the dialysis machine adjacent a second end of the recessed area; and wherein:

said first and second friction pads are adapted to contact the dialyzer and inhibit movement of the dialyzer relative to the surface of the dialysis machine.

16. A dialysis machine having an improved dialyzer holder, said dialyzer holder comprising:

an elongated arm having a first end pivotably attached to the dialysis machine and a second end adapted to selectively pivot away from and toward a surface of the dialysis machine, said elongated arm having a length sufficient to allow the second end to pivot away from the surface of the dialysis machine a sufficient distance to position a dialyzer between the second end and the surface of the dialysis machine;

an elongated rod having a first end fixed to the second end of the elongated arm, said elongated rod extending substantially transverse to the elongated arm and adapted to contact the dialyzer; and means biasing the second end of the elongated arm toward the surface of the dialysis machine to suspend the dialyzer against the surface of the dialysis machine when the dialyzer is positioned between the elongated rod and the surface of the dialysis machine; and wherein:

the elongated rod is adapted to fit within a groove in the surface of the dialysis machine when the dialyzer is not positioned between the elongated rod and the surface of the dialysis machine.

17. A dialysis machine having an improved dialyzer holder, said dialyzer holder comprising:

an elongated arm having a first end pivotably attached to the dialysis machine and a second end adapted to selectively pivot away from and toward a surface of the dialysis machine, said elongated arm having a length sufficient to allow the second end to pivot away from the surface of the dialysis machine a sufficient distance to position a dialyzer between the second end and the surface of the dialysis machine;

an attachment device connected to the second end of the elongated arm and adapted to contact the dialyzer; and means biasing the second end of the elongated arm toward the surface of the dialysis machine to suspend the dialyzer against the surface of the dialysis machine when the dialyzer is positioned between the attachment device and the surface of the dialysis machine; and wherein:

the attachment device includes a rubber block having a rear wall for contacting one of a hollow fiber dialyzer and a plate dialyzer, said rubber block further having a first end wall extending substantially perpendicular from the rear wall for contacting the plate dialyzer, and said rubber block further having a curved second end wall extending substantially tangentially from the rear wall for contacting the hollow fiber dialyzer.

18. A dialysis machine as defined in claim 17 wherein the biasing means comprises a torsion spring.

19. A dialysis machine having an improved dialyzer holder, said dialyzer holder comprising:

a shaft housing fixed to the dialysis machine;

a shaft rotatably attached to the shaft housing;

a torsion spring wrapped around the shaft, said torsion spring having a first end attached to the shaft housing and a second end attached to the shaft to apply a torsional bias to the shaft;

an elongated arm having a first end attached to the shaft, said elongated arm extending substantially transverse to the shaft to allow a second end of the elongated arm to selectively pivot away from and toward a surface of the dialysis machine; and an elongated rod having a first end fixed to the second end of the elongated arm, said elongated rod extending substantially transverse to the elongated arm; and wherein:

the elongated arm has a length sufficient to allow the elongated rod to pivot away from the surface of the dialysis machine a sufficient distance to position a dialyzer between the elongated rod and the surface of the dialysis machine; and the torsion spring applies a sufficient torsional bias to the shaft to bias the elongated rod toward the surface of the dialysis machine and suspend the dialyzer against the surface of the dialysis machine when the dialyzer is positioned between the elongated rod and the surface of the dialysis machine.

20. A dialysis machine as defined in claim 19, further comprising:

a padded surface attached to the elongated rod and adapted to contact the dialyzer and inhibit relative movement between the elongated rod and the dialyzer; and a friction pad positioned on the surface of the dialysis machine to contact the dialyzer and inhibit movement of the dialyzer along the surface of the dialysis machine.

* * * * *

UNITED STATES PATENT AND TRADEMARK OFFICE
Certificate

Patent No. 5,641,144

Patented: June 24, 1997

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Dan L. Hendrickson, Golden, Colo.; Jeff Samson, Boulder, Colo.; Jim Zook, Denver, Colo.; and James M. Brugger, Newburyport, Mass.

Signed and Sealed this Eighth Day of September, 1998.

LESLIE A. BRAUN, *SPE*
Art Unit 3632